July 12, 1949. E. GALLAGHER Plant Pat. 853
ROSE PLANT
Filed May 29, 1947
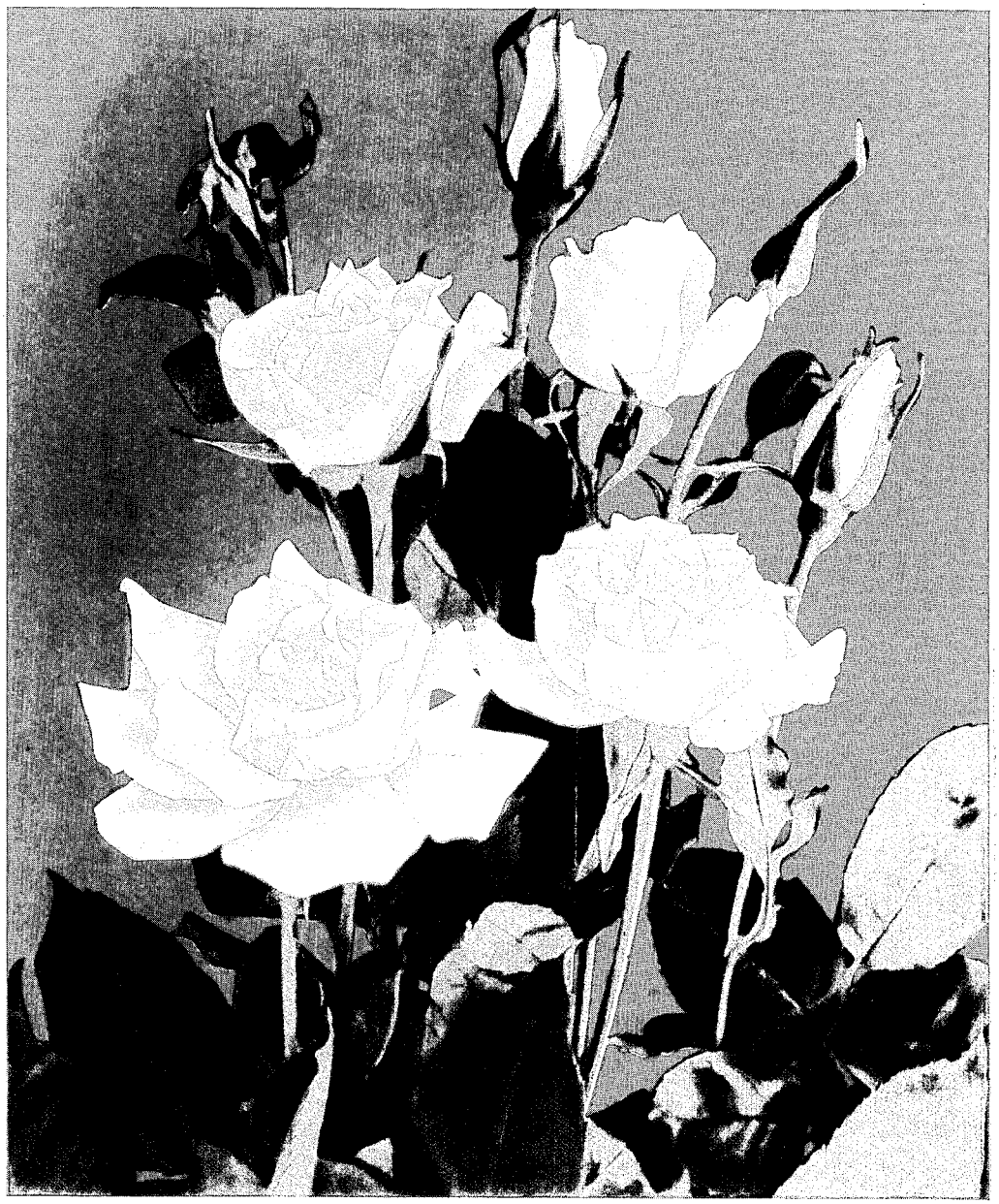
Inventor
Edward Gallagher
By Robbins & Robbins
attorneys Patented July 12, 1949

Plant Pat. 853

UNITED STATES PATENT OFFICE

853

ROSE PLANT

Edward Gallagher, Mount Clemens, Mich., assignor to James E. Carey, Mount Clemens, Mich.

Application May 29, 1947, Serial No. 751,210

1 Claim. (Cl. 47—61)

The present discovery relates to a new and distinct variety of hybrid tea rose plant, originating as a sport of the well-known variety "Briarcliff," some of the better characteristics of which have been passed on to this offspring to produce a novel combination, quite attractive in the line of yellow roses.

This new rose is a strong grower, producing very strong and very long stems on which the large, yellow flowers are borne singly in a setting of very dark and large foliage. The buds of this new variety are very large and perfect in form, thereby adapting the rose particularly for cut flower purposes. Cuttings of this rose grow very strongly in the winter time and dark weather. Another important characteristic is its very strong spicy fragrance.

Asexual reproduction of this new variety shows the foregoing characteristics come true to form and are established.

In the drawings are shown specimens of the new variety, illustrating the bloom at different stages of development and the foliage likewise at different stages.

The following is a detailed description of the new variety, color terminology being in accordance with Ridgway's Color Standard, except where otherwise indicated to have ordinary dictionary significance:

Type: Hardy; tall; greenhouse; sport; for cut flowers.
Class: Hybrid tea.
Breeding: Sport.
*Parent.*—"Briarcliff."
Propagation: Holds its distinguishing characteristics through succeeding propagations by grafting and budding.
Locality where grown: Mount Clemens, Michigan.

*Flower*

Flowers borne: Singly to stem; on strong, long stems.
Quantity of bloom: Free; abundant in greenhouse.
Continuity: Continuous.
Fragrance: Strong; tea; spicy.
Bud:
*Peduncle.*—Long; heavy; erect; stiff; reddish green; smooth; few green prickles.
*Before calyx breaks.*—*Size*—large. *Form*—long, pointed with a conspicuous neck; with slender, much cut foliaceous parts extending beyond the tip of the bud equal to the extent of its length.
*As calyx breaks.*—*Color*—Mustard Yellow, Plate XVI, with Old Rose, Plate XIII, venation.
*As first petal opens.*—*Size*—large. *Form*—pointed. *Color*—outside: Mustard Yellow, Plate XVI, with Old Rose, Plate XIII, venation and Rose tips. Inside: Mustard Yellow, Plate XVI, with Old Rose, Plate XIII, venation more dense.
*Opening.*—Opens up well.

Bloom: Size, when fully open—large; 4" to 5".
*Petalage.*—Double; from 21 to 30 petals.
*Form.*—Full; high center at first; becoming cupped; petals remaining at first and at maturity rolled outward.
Petals: Thick; soft; with inside satiny, velvety, and outside velvety.
*Shape.*—Outside—round with one notch. Intermediate—oval with two notches. Inside—oval with one notch.

This description of a newly opened flower was made from a rose grown in a greenhouse at Mount Clemens, Michigan, in the month of March:

*Color.*—*Outside petal*—outside surface: Mustard Yellow, Plate XVI, very slight Old Rose, Plate XIII; inside surface: Mustard Yellow, Plate XVI, with Old Rose, Plate XIII, venation and Rose apex. *Intermediate petal*—outside surface: Mustard Yellow, Plate XVI, turning pale at edge of petal; inside surface: Mustard Yellow, Plate XVI, turning pale at edge of petal. *Inner petal*—outside surface: very brilliant Mustard Yellow, Plate XVI, quite uniform; inside surface: very brilliant Mustard Yellow, Plate XVI.

This description was made from a rose that was open for three days in a greenhouse at Mount Clemens, Michigan, in the month of March:

*Color.*—*Outside petal*—outside surface: Mustard Yellow, Plate XVI, with slight Old Rose, Plate XIII, venation at tip and turning pale at tip of petal; inside surface: Mustard Yellow, Plate XVI, turning pale at tip of petal. *Inside petal*—outside surface: Mustard Yellow, Plate XVI, pale at tip of petal; inside surface: Mustard Yellow, Plate XVI, pale at tip of petal.
*General color effect.*—Newly opened flower—Mustard Yellow, Plate XVI. Three days open—Brilliant Mustard Yellow, Plate XVI.
*Behavior.*—Persist; fading to white.
*Flower longevity.*—Cut roses grown in greenhouse kept at living room temperatures, five days in March.

*Reproductive organs*

Stamens: Many; arranged regularly about pistils.
Filaments: Medium length; reddish yellow; many with anthers.
Anthers: Medium size; yellow; all open at once.
Pollen: Moderate; yellow.
Pistils: Medium number.
Styles: Uneven; medium length; medium heavy; bunched.
Stigma: Naples Yellow, Plate XVI.
Ovaries: Protruding from calyx.
Hips: Short; flat; gourd-shaped; green; smooth; thick.
Sepals: Permanent; long; spear-shaped; recurved.
*Color.*—Inside—Light Blue Green, Plate VII. Outside—Light Green.
Seeds: Few.

*Plant*

Foliage:
*Leaves.*—Compound of three (near flower) and five to seven (at base) leaflets; abundant; large; heavy; glossy.
*Leaflets.*—Shape—ovoid with apex acute; base—round; margin—simply serrate.
*Color.*—*Mature*—upper surface: dark green; under surface: normal. *Young*—upper surface: Light green; under surface light green.

*Rachis.*—Heavy. Upper side: Smooth; grooved; under side: sparsely smooth.
*Stipules.*—Medium length; medium width; with long points turning out at an angle of more than 45°.
Growth:
*Habit.*—Bushy; upright, branched.
*Growth.*—Free; vigorous.
*Canes.*—Heavy.
*Main stems.*—Green. *Thorns*—few; medium length; hooked downward; with long base. *Prickles and Hairs*—None.
*Branches.*—Green. *Thorns*—few; medium length; hooked downward; with narrow base. *Prickles*—few. *Hairs*—none.
*New Shoots.*—Bright green. *Thorns*—few; medium length; hooked downward; with narrow base. *Prickles and Hairs*—none.

I claim:

A new and distinct variety of rose plant, characterized as to novelty by its habits of growth, the unfading yellow color of its blooms from bud to full blown flower, the perfection and large size of the buds and the large size and dark color of the mature foliage, substantially as shown and described.

EDWARD GALLAGHER.

No references cited.